(12) United States Patent
Ward

(10) Patent No.: US 6,786,424 B1
(45) Date of Patent: Sep. 7, 2004

(54) INSECT REPELLANT ASSEMBLY

(76) Inventor: Matthew Ward, 2630 B W Segerstrom, Santa Ana, CA (US) 19701

( * ) Notice: Subject to any disclaimer, the term of this patent is extended or adjusted under 35 U.S.C. 154(b) by 0 days.

(21) Appl. No.: 10/223,035

(22) Filed: Aug. 16, 2002

(51) Int. Cl.[7] .............................................. A24F 25/00
(52) U.S. Cl. .............................. 239/36; 239/53; 239/55; 239/34
(58) Field of Search ..................... 239/34–60

(56) References Cited

U.S. PATENT DOCUMENTS

| 1,081,148 A | * | 12/1913 | Quayle | 604/308 |
|---|---|---|---|---|
| 2,586,761 A | | 2/1952 | Eskola | |
| 3,098,703 A | | 7/1963 | Snyder et al. | |
| 3,661,326 A | | 5/1972 | Wilson | |
| 3,811,413 A | * | 5/1974 | Scherpenborg | 119/106 |
| 3,844,478 A | | 10/1974 | Davis | |
| 4,031,859 A | * | 6/1977 | Stewart | 119/106 |
| 4,600,146 A | * | 7/1986 | Ohno | 239/53 |
| 4,766,695 A | * | 8/1988 | Harlow | 47/24 |
| 4,900,876 A | * | 2/1990 | Bushman et al. | 19/106 |
| 5,180,107 A | * | 1/1993 | Lindauer | 239/35 |
| 5,665,781 A | * | 9/1997 | Warren | 514/703 |
| 5,875,968 A | * | 3/1999 | Miller et al. | 239/44 |
| 6,086,853 A | * | 7/2000 | Michaels | 424/40 |
| 6,258,857 B1 | * | 7/2001 | Iijima et al. | 424/46 |
| 6,372,242 B1 | * | 4/2002 | Gutierrez | 424/411 |

FOREIGN PATENT DOCUMENTS

GB 2110524 * 6/1983

* cited by examiner

Primary Examiner—Dinh Q. Nguyen

(57) ABSTRACT

A insect repellant assembly for repelling unwanted insects without increasing environmental hazards to humans. The insect repellant assembly includes an housing which elongate and substantially cylindrical, and a repellant mixture positioned within the housing and having an odor which is designed for repelling unwanted insects.

15 Claims, 2 Drawing Sheets

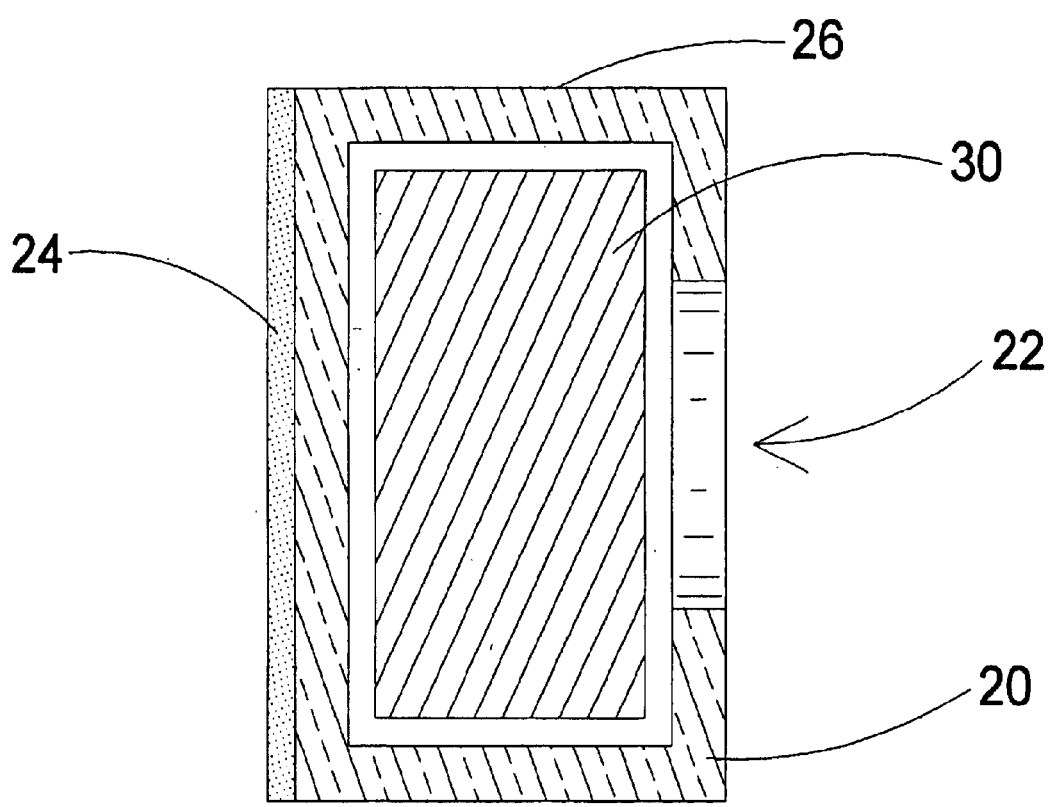

INSECT REPELLANT ASSEMBLY

BACKGROUND OF THE INVENTION

1. Field of the Invention

The present invention relates to insect repellants and more particularly pertains to a new insect repellant assembly for repelling unwanted insects without increasing environmental hazards to humans.

2. Description of the Prior Art

The use of insect repellants is known in the prior art. U.S. Pat. No. 3,661,326 describes a device for use in conjunction with a garbage can lid. Another type of insect repellants is U.S. Pat. No. 3,098,703 having an insecticide for use in containers.

While these devices fulfill their respective, particular objectives and requirements, the need remains for a device that has certain improved features such as the ability to be formed to various surfaces and held in place without any other fixtures.

SUMMARY OF THE INVENTION

The present invention meets the needs presented above by providing a non-toxic insect repellant which may be used in food preparation environments and leaves no insecticide residue.

Another object of the present invention is to provide a new insect repellant assembly that may be attaches to the interior of cabinets and other confined spaces which are known insect traffic areas.

Still another object of the present invention is to provide a new insect repellant assembly that is safe for use around children and does not provide additional environmental toxins.

To this end, the present invention generally comprises an housing which elongate and substantially cylindrical, and a repellant mixture positioned within the housing and having an odor which is designed for repelling unwanted insects.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

The objects of the invention, along with the various features of novelty which characterize the invention, are pointed out with particularity in the claims annexed to and forming a part of this disclosure.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 2 is a schematic cross-sectional view of the present invention.

DESCRIPTION OF THE PREFERRED EMBODIMENT

Figure 1:
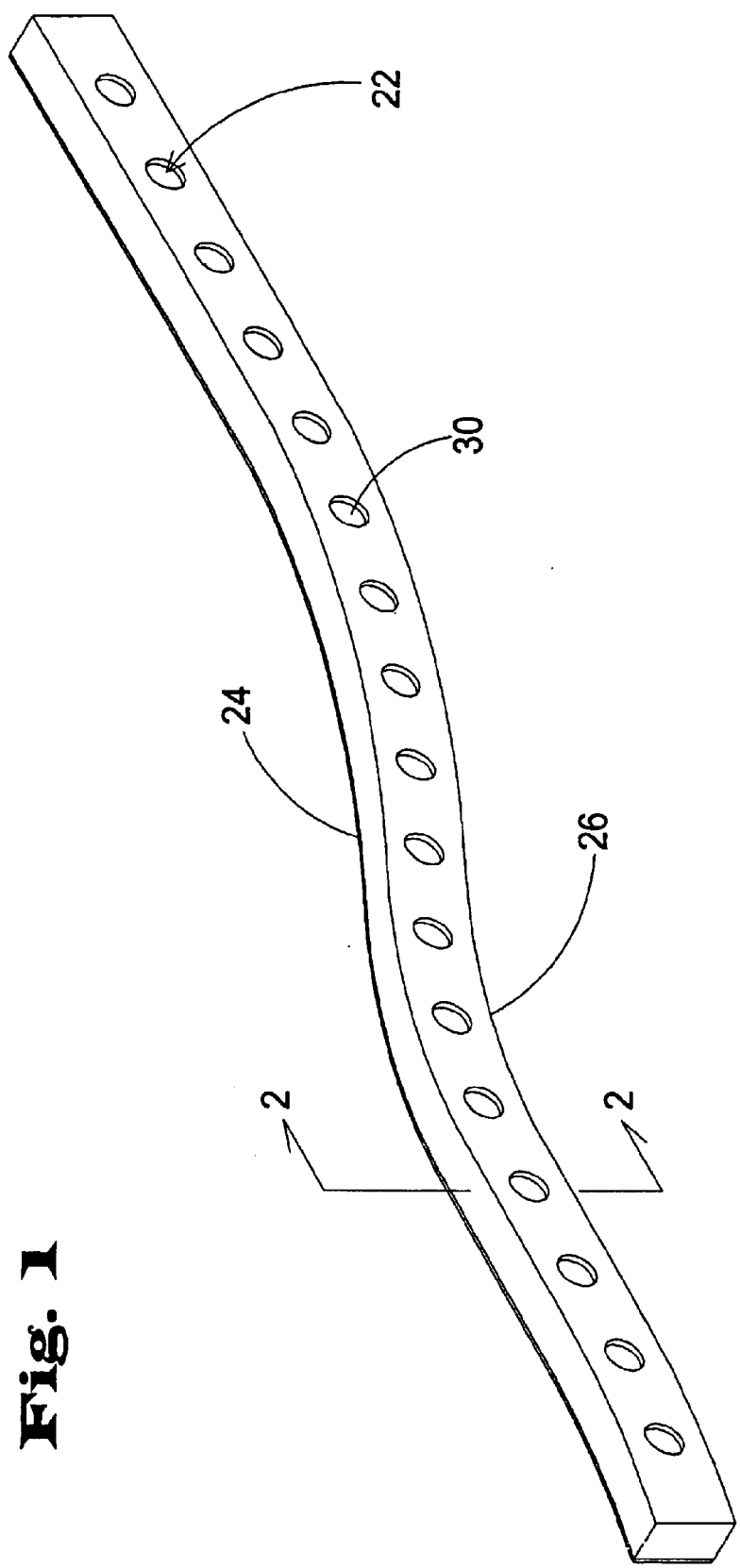
FIG. 1 is a schematic perspective view of a new insect repellant assembly according to the present invention.

With reference now to the drawings, and in particular to FIGS. 1 and 2 thereof, a new insect repellant assembly embodying the principles and concepts of the present invention and generally designated by the reference numeral 10 will be described.

As best illustrated in FIGS. 1 and 2, the insect repellant assembly 10 generally comprises a housing 20 and a repellant mixture 30.

Preferably the housing 20 is elongate and substantially cylindrical. The housing 20 having a perimeter wall 26 defining an interior space. Additionally, the housing 20 may have a cross-section which is square or rectangular.

The repellant mixture 30 designed for repelling unwanted insects. The repellant mixture 30 is positioned within the housing 20 and has an odor which repels insects.

In a preferred embodiment, the housing 20 is substantially transparent for facilitating visual inspection of the repellant mixture 30 such that depletion of the repellant mixture 20 is ascertainable by the user.

Further, the housing 20 may be substantially flexible such that the housing 20 may be conformed to a surface.

An adhesive portion 24 may be coupled to the perimeter wall 26 for facilitating securing the assembly 10 to a surface.

In a further embodiment, each one of a plurality of apertures 22 extends through the perimeter wall 26. The plurality of apertures 22 facilitates transmission of the odor through the housing 20. Thus insects are repelled.

In preferred embodiment the housing 20 has a diameter of in the range between 0.125 and 1.0 inches. In a more preferred embodiment, the housing 20 has a diameter of approximately 0.25 inches.

In a further embodiment the housing 20 has a length of approximately 6 inches and is designed for residential use.

In an alternate embodiment the housing 20 has a length of approximately 100 feet and is designed for commercial use.

Most preferably, the repellant mixture 30 comprises Citronella oil and Glycerine lotion.

In use, the assembly is positioned in known or suspected insect traffic areas or in areas the user which to remain free of unwanted insects, including cockroaches. The assembly is left in place until the repellant mixture has been depleted.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. An insect repellant assembly comprising:
   an housing being elongate and substantially cylindrical, said housing having a perimeter wall defining an interior space;
   a repellant mixture adapted for repelling unwanted insects, said repellant mixture being positioned within said housing, said repellant mixture having an odor which repels insects;
   said housing being substantially transparent for facilitating visual inspection of said repellant mixture such that depletion of said repellant mixture is ascertainable;

said housing being substantially flexible such that said housing may be conformed to a surface;

an adhesive portion coupled to said perimeter wall for facilitating securing said assembly to an surface; and a plurality of apertures extending through said perimeter wall, said plurality of apertures facilitating transmission of the odor through said housing whereby insects are repelled.

2. The assembly of claim 1, wherein said housing having a diameter of in the range between 0.125 and 1.0 inches.

3. The assembly of claim 1, wherein said housing having a diameter of approximately 0.25 inches.

4. The assembly of claim 1, wherein said housing having a length of approximately 6 inches.

5. The assembly of claim 1, wherein said housing having a length of approximately 100 feet.

6. The assembly of claim 1, wherein said repellant mixture comprises Citronella oil and Glycerine lotion.

7. An insect repellant assembly comprising:

an housing being elongate and substantially tubular, said housing having a perimeter wall defining an interior space;

a repellant mixture adapted for repelling unwanted insects, said repellant mixture being positioned within said housing, said repellant mixture having an odor which repels insects; and fastening means on a first side of said housing for fastening said housing to a surface such that said housing is supported on the surface;

wherein said housing further comprises a plurality of apertures extending through said perimeter wall for facilitating transmission of the odor through said housing to repel insects;

wherein said fastening means is located on a first side of said housing and a second side of said housing, said first side of said housing being located opposite of said second side of said housing such that said plurality of apertures are positionable away from the surface when said housing is fastened to the surface by said fastening means.

8. The assembly of claim 7, wherein said housing being substantially transparent for facilitating visual inspection of said repellant mixture such that depletion of said repellant mixture is ascertainable.

9. The assembly of claim 7, wherein said housing being substantially flexible such that said housing may be conformed to a surface.

10. The assembly of claim 7, wherein said repellant mixture comprises Citronella oil and Glycerine lotion.

11. The assembly of claim 7, wherein said fastening means further comprises an adhesive portion coupled to said perimeter wall for facilitating securing said assembly to an surface.

12. The assembly of claim 7, wherein said housing having a diameter of in the range between 0.125 and 1.0 inches.

13. The assembly of claim 7, wherein said housing having a diameter of approximately 0.25 inches.

14. The assembly of claim 7, wherein said housing having a length of approximately 6 inches.

15. The assembly of claim 7, wherein said housing having a length of approximately 100 feet.

* * * * *